Jan. 18, 1955 G. DE RUITER Plant Pat. 1,341
ROSE PLANT
Filed April 8, 1954
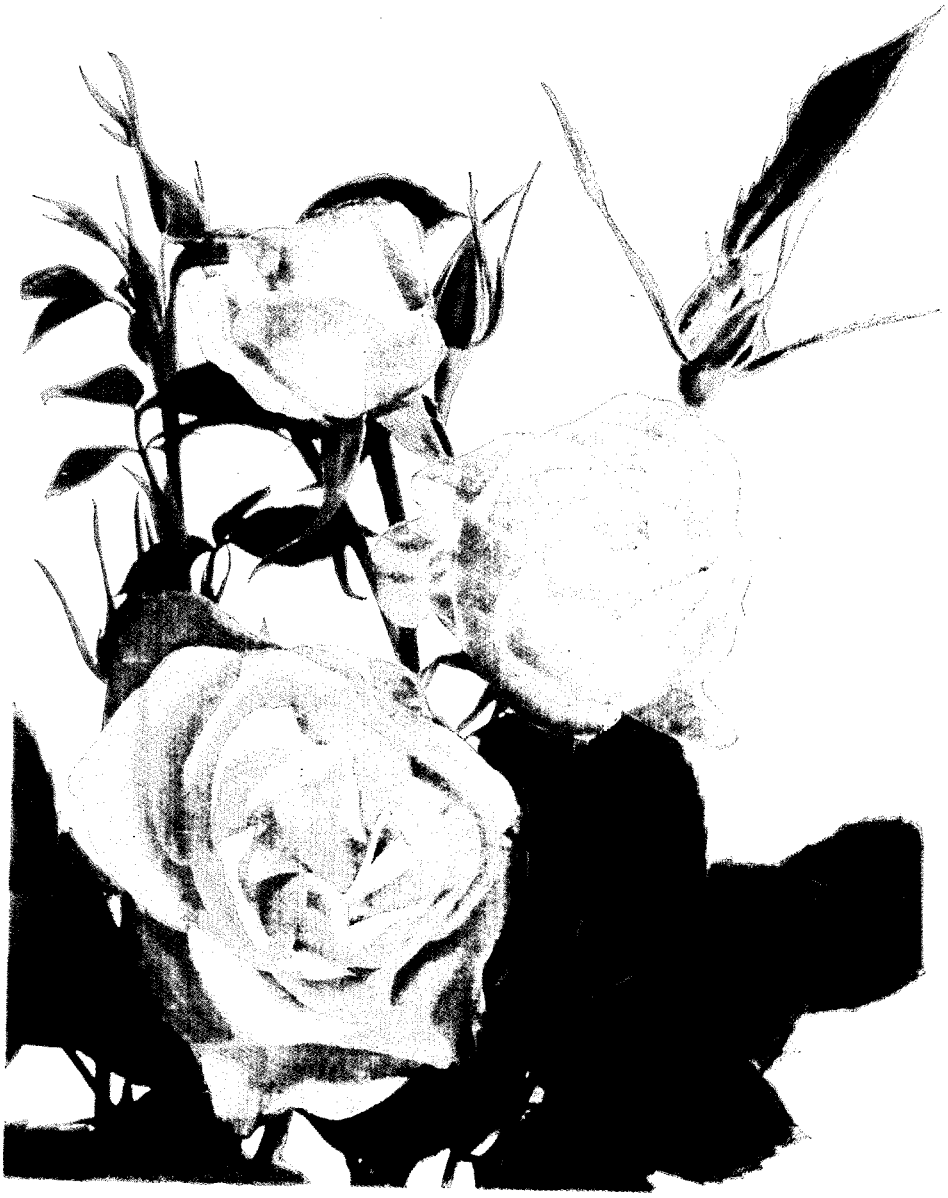
Inventor.
Gerrit de Ruiter
By: Robb & Robb
Attorneys.

United States Patent Office

Plant Pat. 1,341

Patented Jan. 18, 1955

1,341

ROSE PLANT

Gerrit De Ruiter, Hazerswoude, Netherlands, assignor to The Conard-Pyle Company, West Grove, Pa., a corporation of Pennsylvania Application April 8, 1954, Serial No. 421,993

1 Claim. (Cl. 47—61)

The present invention relates to a new and distinct variety of rose plant of the large-flowered hybrid polyantha class, commonly called floribunda, which was originated by me by crossing the variety "Better Times" (Plant Patent No. 23) with an unnamed and unpatented polyantha seedling.

As the result of this breeding, I have produced a new variety of rose which is particularly characterized by its distinctive color, said color being a deep tone of Crimson Carmine, but when observed from an angle has a bluish appearance which is not apparent when viewed directly. In addition to this characteristic, the plants of my new variety are vigorous and very free-blooming, and my new variety also has better than average resistance to blackspot.

The foregoing characteristics, taken together, represent an unusual and desirable combination of features which distinguishes my new variety from its parents, as well as from all other varieties of its class.

Asexual reproduction of my new variety by budding, as performed at Hazerswoude, Holland, and also at West Grove, Pennsylvania, shows that the foregoing characteristics and distinctions come true to form and are established and transmitted through succeeding propagations.

The accompanying drawing shows typical specimens of the flowers and foliage of my new variety in different stages of development and as depicted in color as nearly true as it is reasonably possible to make the same in a color illustration of this character.

The following is a detailed description of my new variety, with color terminology in accordance with Ridgway's Color Standards and Nomenclature (hereinafter abbreviated as "Ridgway"), and with the Royal Horticultural Society Color Chart (hereinafter abbreviated as "Royal") where the Ridgway Chart is inadequate, except where general color terms of ordinary dictionary significance are obvious:

Type: Hardy; bush; outdoor; seedling; for cut-flowers and for garden decoration.
Class: Hybrid polyantha.
Breeding: Seedling.
*Seed parent.*—"Better Times."
*Pollen parent.*—An unnamed polyantha seedling.
Propagation: Holds its distinguishing characteristics through succeeding propagations by budding.

FLOWER

Locality where grown and observed: West Grove, Pennsylvania.
Flowers borne: Several to stem; in irregular cluster; on medium length stems of normal strength.
Quantity of bloom: Free, outdoors.
Continuity: Continuous.
Fragrance: Moderate.
Bud:
*Peduncle.*—Medium length; erect; rough; numerous red prickles. Color—Pompeian Red, Plate XIII (Ridgway).
*Before calyx breaks.*—Size—small. Form—short; globular; with a conspicuous neck; with foliaceous appendages on the surface of the bud; with slender, much-cut, bristle-like foliaceous parts extending beyond the tip of the bud equal to 1½ times its length.
*As calyx breaks.*—Color—Oxblood Red, Tone 3, Plate 94 (Royal).

*As first petal opens.*—Size—medium. Form—medium length; globular. Color: Outside—French Purple, Tone 4, Plate 161 (Royal), shading to Carmine Purple, Tone 3, Plate 156 (Royal); sometimes overlaid with patches of Oxblood Red, Plate I (Ridgway). Inside—French Purple, Tone 3, Plate 161 (Royal); shading to Currant Red, Tone 2, Plate 115 (Royal); base Cadmium Yellow, Tone 1, Plate 23 (Royal).
*Opening.*—Opens up well.
Bloom:
*Size* (when fully open).—Medium; from 3 inches to 3½ inches.
*Petalage.*—Double; from 24 to 27 petals; arranged regularly.
*Form.*—Open-cupped at first; remaining open-cupped; petals being at first loosely rolled outward, and remaining rolled outward through maturity.
Petals: Medium thickness; leathery; with inside velvety and outside satiny.
*Shape.*—Outer petals—obovate, usually with 1 notch, but occasionally none. Intermediate petals—obovate, with 1 notch. Inner petals—obovate, with 1 notch.

This description of a newly opened flower was made from a rose grown outdoors in the month of September, at West Grove, Pennsylvania:
*Color.*—Outer petal: outside surface—evenly distributed Lilac Purple, Tone 4, Plate 160 (Royal); inside surface—Geranium Red, Tone 4, Plate 111 (Royal), shading to Crimson Carmine, Tone 3, Plate 159 (Royal). Intermediate petal: outside surface—Lilac Purple, Tone 3, Plate 160 (Royal); inside surface—entirely Crimson Carmine, Tone 3, Plate 159 (Royal). Inner petal: outside surface—Lilac Purple, Tone 2, Plate 160 (Royal); often with a white streak or streaks radiating out from base; inside surface—Crimson Carmine, Tone 3, Plate 159 (Royal).

This description was made from a rose that was open for three days outdoors in the month September, at West Grove, Pennsylvania:
*Color.*—Outer petal: outside surface—evenly Crimson Carmine, Tone 3, Plate 159 (Royal); sometimes shaded at outer edges and at center of petal with a color darker than Crimson Carmine, Tone 4, Plate 159 (Royal); inside surface—deeper color than Crimson Carmine, Tone 4, Plate 159 (Royal), shading into Crimson Carmine, Tone 4, Plate 159 (Royal), and then to Lilac Purple, Tone 1, Plate 160 (Royal). Inner petal: outside surface—an even tone of Crimson Carmine, Tone 2, Plate 159 (Royal) over entire surface, except for an occasional white streak from base to apex; inside surface—Crimson Carmine, Tone 4, Plate 159 (Royal), shading into Crimson Carmine, Tone 1, Plate 159 (Royal) towards base.
*General color effect.*—Newly opened flower—an iridescent Crimson Carmine, of a deeper tone than Tone 4, Plate 159 (Royal). 3-days open—an iridescent Crimson Carmine, Tone 4, Plate 159 (Royal), having a bluish tinge when viewed in indirect light.
*Behavior.*—Drop off cleanly.
*Flower longevity.*—On bush in garden—4 days in September. Cut roses grown outdoors and kept at living-room temperatures—4 days in September.

REPRODUCTIVE ORGANS

Stamens: Few to medium number; arranged regularly about pistils.
Filaments: Few without anthers; medium length. Color—Pinard Yellow, Plate IV (Ridgway).
Anthers: All open at once; medium size; occasionally an anther fused with a petaloid. Color—Buff Yellow, Plate IV (Ridgway).
Pollen: Moderate abundance. Color—Wax Yellow, Plate XVI (Ridgway).
Pistils: Medium number.

Styles: Uneven; medium length; medium caliper; bunched.
Stigma: Color—Citron Yellow, Plate XVI (Ridgway).
Ovaries: All enclosed in calyx.
Hips: None.
Sepals: Permanent; long; straight; spear-shaped.
Seeds: None.

PLANT

Foliage:

*Leaves.*—Compound of 5 or 7 leaflets; normal abundance; medium size; leathery, with slight gloss.

*Leaflets.*—Shape—oval, with apex acute. Base—Acute, but sometimes obtuse. Margin—Simply serrate.

*Color.*—Mature: upper surface—dark dull Yellow-Green, Plate XXXII (Ridgway); under surface—Asphodel Green, Plate XLI (Ridgway), tinged with Acajou Red, Plate XIII (Ridgway). Young: upper surface—Victoria Lake, Plate I (Ridgway); under surface—Livid Brown, Plate XXXIX (Ridgway).

*Rachis* (the supporting stem of the compound leaf).—Upper side—grooved; prickly on margins; hairy at bottom of groove. Under side—sparsely prickly and thorny.

*Stipules.*—Medium length; moderately narrow; with long points turning out at a variable angle.

*Disease resistance.*—Resistant to blackspot as compared with other varieties grown under comparable cultural conditions at West Grove, Pennsylvania.

Growth:

*Habit.*—Bushy; much-branched.

*Growth.*—Vigorous.

*Canes.*—Medium caliper.

*Main stems.*—Color—Biscay Green, Plate XVII (Ridgway). Thorns—several; medium length; straight; pointed downward; with short, broad, oval base. Prickles—several. Hairs—none.

*Branches.*—Color—Light Bice Green, Plate XVII (Ridgway). Thorns—Many; medium length; straight; pointed slightly downward; with medium length, oval base. Prickles—several red prickles towards top of plant. Hairs—none.

*New shoots.*—Color—Dark Vinaceous, Plate XXVII (Ridgway). Thorns—several; medium length; straight; with medium length, oval base. Prickles—many; reddish color. Hairs—none.

I claim:

A new and distinct variety of rose plant of the hybrid polyantha class, substantially as herein shown and described, characterized particularly as to novelty by its vigorous and very free-blooming habit, by its better-than-average resistance to blackspot, and by the distinctive deep tone of Crimson Carmine general color tonality of its blooms which have a bluish tinge when viewed indirectly.

No references cited.